United States Patent [19]

Wulff et al.

[11] Patent Number: 5,275,758
[45] Date of Patent: Jan. 4, 1994

[54] PRODUCTION OF ULTRAFINE SUSPENSIONS OF BISPHENOL, SODIUM HYDROXIDE AND WATER

[75] Inventors: Claus Wulff, Krefeld; Reinhard Schomäcker, Leverkusen; Jürgen Kadelka, Krefeld; Jürgen Heuser, Krefeld; Günther Weymans; Konrad Hable, both of Leverkusen, all of Fed. Rep. of Germany

[73] Assignee: Bayer Aktiengesellschaft, Leverkusen, Fed. Rep. of Germany

[21] Appl. No.: 940,254

[22] Filed: Sep. 1, 1992

[30] Foreign Application Priority Data

Sep. 5, 1991 [DE] Fed. Rep. of Germany ....... 4129546

[51] Int. Cl.$^5$ ............................................. B01J 13/00
[52] U.S. Cl. ............................. 252/314; 252/183.13; 252/311; 528/196
[58] Field of Search ................ 252/183.13, 311, 314

[56] References Cited

U.S. PATENT DOCUMENTS

| | | | |
|---|---|---|---|
| 1,637,475 | 8/1927 | Davis et al. | 252/314 X |
| 2,021,143 | 11/1935 | Calcott et al. | 252/314 |
| 2,284,023 | 5/1942 | Scripture, Jr. | 252/314 |
| 2,684,949 | 7/1954 | McMillan et al. | 252/314 |
| 3,635,834 | 1/1972 | Cilento et al. | 252/314 |
| 3,945,969 | 3/1976 | Horn et al. | 526/64 |
| 4,122,112 | 10/1978 | Koda et al. | 558/268 |
| 4,338,470 | 7/1982 | Granjon et al. | 568/723 |
| 4,447,655 | 5/1984 | Mendiratta | 568/724 |
| 4,737,573 | 4/1988 | Silva et al. | 528/371 |
| 4,810,813 | 3/1989 | Kosky et al. | 558/281 |
| 4,847,352 | 7/1989 | Weston et al. | 528/196 |
| 4,949,456 | 9/1990 | Ashida et al. | 528/371 |
| 5,011,967 | 4/1991 | Silva et al. | 558/281 |

FOREIGN PATENT DOCUMENTS

| | | |
|---|---|---|
| 341225 | 1/1978 | Austria . |
| 306838 | 3/1989 | European Pat. Off. . |
| 1409614 | 10/1975 | United Kingdom . |

*Primary Examiner*—Richard D. Lovering
*Attorney, Agent, or Firm*—Joseph C. Gil; Aron Preis

[57] ABSTRACT

The invention relates to ultrafine suspensions of bisphenol, sodium hydroxide and water for the production of polycarbonates by the two-phase interfacial process. According to the invention, these suspensions are prepared by cooling bisphenolate concentrations near the solubility limit in aqueous sodium hydroxide with intensive mixing at relatively high temperatures and precipitating bisphenolate or more bisphenolate in the form of fine droplets during the cooling process. The ultrafine suspensions provide for a high volume/time yield in the interfacial reaction.

1 Claim, No Drawings

PRODUCTION OF ULTRAFINE SUSPENSIONS OF BISPHENOL, SODIUM HYDROXIDE AND WATER

The two-phase interfacial process has been successfully used for the production of polycarbonates on an industrial scale. As a continuous process, it is generally attended by the disadvantage that, to accelerate the reaction and to improve phase separation, more phosgene has to be used than is necessary for the product balance. The excess phosgene is then degraded in the synthesis in the form of secondary products, for example additional sodium chloride or alkali metal carbonate compounds.

There has been no shortage of attempts to reduce this excess of phosgene. Some of the attempted improvements have been based on the use of special bisphenolate solutions. In addition, a number of different metering and reaction procedures have been described in the prior art.

Thus, DOS-2 305 144 describes a process for the continuous production of polycarbonates in which the two reactive phases are combined in a mixing zone in the presence of amines under substantially oil-in-water emulsion conditions and the phosgenation reaction takes place after mixing in a reaction zone. Special flow arrangements are said to ensure that the volume/time yield of the reaction is increased. The disadvantage of this known process lies in the large quantity of aqueous phase which supports phosgene secondary reactions.

According to DOS 2 353 939, the properties of a polycarbonate produced by the two-phase interfacial process are supposed to be able to be improved by control of the reaction by pH regulation. The disadvantage of this known process lies in the phosgene excess used, in addition to which the process is not continuous.

According to the teaching of EP 0 282 546, condensates terminated by chloroformyl groups are said to be produced in high phosgene yields by the two-phase interfacial process by the simultaneous and continuous introduction of a stable diphenol/water/sodium hydroxide suspension and phosgene into an organic phase and subsequent isolation of the reaction product. pH values of 2 to 5 are adjusted during the reaction. The disadvantage of this process lies in the technical difficulties involved in metering of the suspension and in the low pH value which considerably increases the phosgenation time. Polycondensation measures are not described in this document.

According to EP-0 263 432, condensates terminated by chloroformyl groups or polycarbonates can be produced from aqueous diphenolate solution and organic solution by incorporation in a heterogeneous mixture at pH values of 8 to 11, at temperatures of 15 to 50° C. and with a phosgene excess of at least 10 mol-% phosgene and continuing the phosgenation reaction with simultaneous introduction of alkali metal or alkaline earth metal hydroxides. Preferred water-to-oil phase ratios are 0.4 to 1:1, water being subsequently introduced.

According to DOS-2 725 967, it is favorable to the phosgene yield of a continuous process initially to combine the aqueous phase and the organic phase containing phosgene in solution in a tube and subsequently to introduce the combined phases into a reactor of the tank type. The residence time in this tube is between 0.5 and 15 seconds. The phosgene excess of the reaction is at least 10 mol-%. The disadvantage of this known process lies in the still extremely high phosgene excess. Another disadvantage is that the phosgenation reaction takes place at unfavorable phase ratios (oil to water = 0.2 to 1) to ensure that the two phases can be safely separated on completion of the reaction.

According to EP 0 306 838 A2, the phosgenation reaction is monitored in situ using an automatic Cl detector. Carrying out the process in this way suppresses variations in the mechanism of the reaction and, apparently, improves the technical properties of the polycarbonates to a considerable extent. The basic concept of the process lies in the return of unreacted diphenolate to the process. However, the disadvantage of the process lies in the phosgene secondary reactions which are also reflected in this recycling measure.

It is known from EP 0 339 503 A2 that the phosgene secondary reactions can be increased in particular by the presence of a high initial sodium hydroxide concentration. In this document, therefore, the diphenol/sodium hydroxide/water solution is combined with the organic phase in an alkali:hydroxy ratio below 2:1 (less alkali metal hydroxide), oligomers having a molecular weight of 300 to 3,000 g/mol being formed in this first stage of the reaction. The water-to-oil phase ratios are greater than 1. In addition, the phosgene secondary reactions are still extremely unfavorable.

According to EP 0 304 691 A2, a fine emulsion (obtained by intensive mixing) is favorable to the course of the reaction in the two-phase interfacial process, albeit with a very high phosgene excess (20 to 100 mol-% excess). The high phosgene excess provides for good phase separation despite intensive mixing of the emulsion at the beginning of the reaction. However, the phosgene yield is extremely unfavorable.

A process for the production of reaction products of phosgene and dihydroxyphenols is described in WO 88/01 996. The introduction of special bisphenol suspensions is said to prevent phosgene secondary reactions and to make the process easier to carry out. The starting material used in this known process is a mixture of crystalline bisphenol A, alkali metal hydroxide and water in certain ratios and is subsequently converted by vigorous stirring into a suspension which remains stable for at least 30 minutes and which is continuously or discontinuously added, for example, in the synthesis of polycarbonates. Preferred compositions of the suspension are 47.9 to 52.0% bisphenol A, 52 to 47.9% water and 0.01 to 0.2% alkali metal hydroxide. In addition, compositions of 20 to 50% bisphenol A, 8 to 16% alkali metal hydroxide and 40 to 70% water can generally be used. Typical phosgenation temperatures are in the range from 14 to 40° C. The suspensions are not ultrafine suspensions and the production time is too long, particularly for use in a continuous reaction, because the crystalline bisphenol A particles first have to be "partly dissolved" in the suspension.

US-PS 4,447,655 describes a special purification process for bisphenol A in which bisphenol A suspensions are washed with an organic washing medium in a continuous multiple-plate countercurrent extraction column. It is pointed out in this document regarding the suspension that the ratio of water to bisphenol A is not important to the washing process. The suspensions are prepared by stirring water at low temperature into a bisphenol melt, so that the mixture is cooled to temperatures of 60 to 70° C., and subsequently forming crystals from the aqueous solution by continued cooling. These crystals may be subjected to the described purification.

According to AT 341 225, bisphenolate suspensions have advantages when used in the form of aqueous solutions in the two phase interfacial process because high-quality polycarbonates can be obtained from them in a high raw-material yield. In addition, these suspensions have the advantage that only a little water is used in the reaction.

Accordingly, although there are a number of advantages in using bisphenolate suspensions in the two-phase interfacial process ranging from the improved phosgene yield to an increase in polycarbonate quality, the reproducible production of such suspensions and their introduction into the synthesis are still attended by disadvantages.

It has now surprisingly been found that these disadvantages can be avoided if the bisphenolate suspensions are produced in a-finer form than before by a special temperature program.

The present invention relates to a process for the production of ultrafine suspensions based on 2,2-bis-(4-hydroxyphenyl)-propane (=bisphenol A, "BPA"), sodium hdyroxide and water, characterized in that a) a melt of bisphenol A is combined with sodium hydroxide and water with intensive mixing (mixing energy >0.5 watt/liter), b) a temperature of at least 60° C. and at most 90° C. being established in at most 1 minute after mixing, optionally by cooling, and c) the ratios of bisphenol A to NaOH are selected so that between 1.5 and 2.2 mol NaOH are used per mol bisphenol A and 15 parts by weight to 40 parts by weight of the sum of BPA and NaOH are present per 100 parts by weight water and d) at most 50% of the BPA used, optionally in the form of its alkali metal salt, are precipitated at those temperatures and e) the aqueous solution is subsequently cooled with further vigorous mixing (mixing energy>0.5 watt/liter) to temperatures of 10 to 35° C. in times of 1 second to 30 minutes, an opaque ultrafine suspension being formed.

The present invention also relates to the ultrafine suspensions obtainable by the process according to the invention.

The present invention also relates to the use of the ultrafine suspensions obtainable in accordance with the invention for the production of polycarbonates by the interfacial process.

The bisphenol A melt is generally present at temperatures just above the melting point, i.e. between 160 and 200° C. Contact with oxygen is avoided as far as possible during this process step and all following process steps. By applying high mixing energies, generally of more than 0.5 watt/liter, preferably more than 1 watt/liter and, more preferably, more than 1.2 watt/liter, the hot melt is ultrafinely dispersed in the absence of oxygen in the sodium hydroxide which is present at temperatures of 20 to 70° C. and optionally already diluted with water and to which more water may subsequently be added to establish the necessary stoichiometry. Mixing may be carried out in any units which enable the bisphenol melt to be uniformly and rapidly cooled in a short time in the presence of sodium hydroxide under the effect of high mixing energy. Accordingly, suitable mixing elements are, in particular, two-component nozzles in which aqueous sodium hydroxide solution and bisphenol melt are combined, optionally under the pressure of an inert gas, and expanded in a vessel.

Intensive stirring of the mixture is continued in this vessel, temperatures of at least 60° C. to at most 90° C. being established in the vessel. In the continuous production of the suspensions according to the invention, the vessel is optionally slightly cooled to establish the desired temperature range, depending on the dissipation of heat.

The ratios in which the starting materials are mixed before the beginning of measure e) according to the invention are selected so that between 1.5 and 2.2 mol NaOH, preferably less than 2.1 mol NaOH and, more preferably, between 1.8 and 2.05 mol NaOH are used per mol bisphenol A. In general, between 15 parts by weight and 40 parts by weight and preferably between 15 and 35 parts by weight of the sum of bisphenol A and NaOH are used per 100 parts by weight water. In addition, the bisphenol concentrations in these molar ratios are selected so that at most 50% of the bisphenol used and preferably between 2 and 20% has precipitated as fine crystals before the beginning of measure e). The particles precipitated may be both pure bisphenol A and a mixture of bisphenol A and bisphenolate and also pure bisphenolate.

In measure e), the suspension is cooled with continued vigorous stirring and, at the same time, cooling to temperatures of 10 to 35° C. in times of 1 second to 30 minutes and preferably in times of about 1 minute, more sodium bisphenolate being precipitated in the form of very fine particles.

The suspension formed is combined, generally with gentle mixing, with an organic solution containing phosgene for the polycarbonate reaction, the organic solution preferably consisting of such solvents as methylene chloride, monochlorobenzene or mixtures of both and the solution containing between 1.05 mol and 1.35 mol and preferably less than 1.25 mol phosgene per mol bisphenol A. After phosgenation, the solution is reacted off to polycarbonate in the presence of known catalysts, chain terminators and more sodium hydroxide solution in known quantities and the polycarbonate is isolated from the emulsion in known manner.

EXAMPLE

The following Example was carried out in a Buchi 1 liter laboratory reactor equipped with a paddle stirrer. The reactor is equipped with a cooling jacket through which the heat of reaction can be dissipated as required. Connected to the reactor is a temperature-controlled storage vessel from which aqueous NaBPA solution can be suddenly introduced into the reactor.

220 g methylene chloride and 220 g monochlorobenzene are introduced into the reactor and 35.6 g (0.36 mol) phosgene are dissolved therein with vigorous stirring at room temperature.

215 g water and 24 g sodium hydroxide (0.6 mol) are heated to around 60° C. in the storage vessel. 68.5 g bisphenol A (0.3 mol) at a temperature of 170° C. are sprayed into this solution in 10 seconds with intensive stirring (mixing energy 1.6 watt/liter) in an inert gas (nitrogen) atmosphere under a pressure of 10 bar. The solution undergoes slight heating. The sodium bisphenolate solution was then cooled to 25° C. with continued vigorous stirring (mixing energy at least 1.5 watt/liter). A sample of this solution was taken, sodium bisphenolate precipitating in the form of a very fine deposit a few minutes after the end of stirring at the temperature of 25° C. The suspension was suddenly introduced into the reactor from the storage vessel with continued vigorous stirring. The temperature of the emulsion formed rose to around 50 to 53° C. during the phosgenation. After 10 minutes, 0.6 g phenol (0.0063 mol) was introduced into 8 g 25% sodium hydroxide (0.05 mol). After 30 minutes, 1.36 g of a 5% N-ethyl piperidine solution in methylene chloride and 19.4 g 50% sodium hydroxide solution (0.11 mol) were added. The temperature was kept at 30° C. After another 10 minutes, the reaction was terminated by switching off the stirrer and separating the emulsion.

Analytical data molecular weight Mn of the polycarbonate: 16,000 g/mol bisphenol A content of the aqueous phase: below 1 ppm (!)

carbonate content of the aqueous phase: 1.1%.

Carrying out the reaction as described above produced a high phosgene yield and a readily separable emulsion.

We claim:

1. A process for the production of ultrafine suspensions based on 2,2-bis- )-propane (=bisphenol A, "BPA"), sodium hydyroxide and water, characterized in that
  a) a melt of bisphenol A is combined with sodium hydroxide and water with intensive mixing (mixing energy 0.5 watt/liter),
  b) a temperature of at least 60° C. and at most 90° C. being established in at most 1 minute after mixing, optionally by cooling, and
  c) the ratios of bisphenol A to NaOH are selected so that between 1.5 and 2.2 mol NaOH are used per mol bisphenol A and 15 parts by weight to 40 parts by weight of the sum of BPA and NaOH are present per 100 parts by weight water and
  d) at most 50% of the BPA used, optionally in the form of its alkali metal salt, are precipitated at those temperatures and
  e) the aqueous solution is subsequently cooled with further vigorous mixing (mixing energy>0.5 watt/liter) to temperatures of 10 to 35° C. in times of 1 second to 30 minutes, an opaque ultrafine suspension being formed.

* * * * *